United States Patent [19]

Kubo et al.

[11] 4,143,061
[45] Mar. 6, 1979

[54] 3-(α,α-DIMETHYLBENZYL)UREA COMPOUNDS, COMPOSITIONS, AND THEIR USE AS HERBICIDES

[75] Inventors: Hiroshi Kubo; Takashi Isono, both of Yokohama; Nansho Seki, Tokyo; Noriyuki Sato, Yokohama, all of Japan

[73] Assignee: Showa Denko Kabushiki Kaisha, Tokyo, Japan

[21] Appl. No.: 755,281

[22] Filed: Dec. 29, 1976

[30] Foreign Application Priority Data

Dec. 30, 1975 [AU] Australia .................. 87946/75

[51] Int. Cl.² ............... A01N 9/20; C07C 127/17
[52] U.S. Cl. ............... 260/453 RW; 71/119; 71/120; 260/553 A
[58] Field of Search ....... 260/553 A, 453 R, 453 RN; 71/119, 120

[56] References Cited

U.S. PATENT DOCUMENTS

| | | | |
|---|---|---|---|
| 2,795,610 | 6/1957 | Gerjovich | 260/553 A |
| 3,174,991 | 3/1965 | Steinbrunn | 260/553 A X |
| 3,388,158 | 6/1968 | Surrey | 260/553 A |
| 3,483,296 | 12/1969 | Martin et al. | 260/553 A X |
| 3,799,964 | 3/1974 | van Daalen et al. | 71/120 X |
| 3,813,436 | 5/1974 | Duerr et al. | 260/553 A |
| 3,972,909 | 8/1976 | Kubo et al. | 71/120 X |

FOREIGN PATENT DOCUMENTS

| | | | |
|---|---|---|---|
| 44-311 | 1/1969 | Japan | 71/119 |
| 7242493 | 10/1972 | Japan | 71/120 |
| 7335454 | 10/1973 | Japan | 71/120 |
| 1332102 | 10/1973 | United Kingdom. | |
| 202927 | 9/1967 | U.S.S.R. | 260/553 A |

OTHER PUBLICATIONS

Aya et al., CA 83:159153n and 159154p, (1975), 6/21/75.
Ishii et al., CA 84:160603m.
Takematu et al., CA 80:11215b, (1974).

*Primary Examiner*—Thomas Waltz
*Attorney, Agent, or Firm*—Sughrue, Rothwell, Mion, Zinn and Macpeak

[57] ABSTRACT

A compound of the general formula (I):

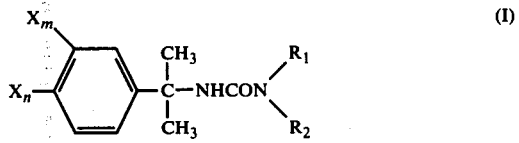

wherein X is halogen or trifluoromethyl, n and m are 0 or 1, $R_1$ is lower $C_1 - C_2$ alkyl or $C_1 - C_2$ alkoxy and $R_2$ is $C_4 - C_5$ alkyl, cyclohexyl, or phenyl, methods of the preparation thereof, herbicidal compositions containing same and a method for controlling weeds using the same.

2 Claims, No Drawings

3-(α,α-DIMETHYLBENZYL)UREA COMPOUNDS, COMPOSITIONS, AND THEIR USE AS HERBICIDES

BACKGROUND OF THE INVENTION

1. Field of the Invention

This invention relates to substituted 3-(α,α-dimethylbenzyl)urea compounds, to methods of the preparation thereof, to herbicidal compositions containing such compounds, and to a method for controlling weed growth employing these compounds and compositions.

2. Description of the Prior Art

Various urea derivatives have been proposed as herbicides since fenuron, monuron, diuron, etc., were developed at the beginning of the 1950's. However, most of the compounds whose herbicidal activities have been confirmed and which have been practically used are those having a phenylurea type chemical structure. Very few compounds are of the aralkylurea type, as described in Floyd M. Ashton et al., *Table 21-1, Urea Type Herbicides in General Use, Mode of Action of Herbicides*, Wiley-Interscience, p. 369. That is, most of the urea derivatives presently used as herbicides have a chemical structure where a phenyl group or a substituted phenyl group is directly attached to at least one of the nitrogen atoms of a urea skeleton.

Hitherto, some of the prior art references describe aralkylurea type herbicides, for example, U.S. Pat. Nos. 3,388,158, 3,483,296 and 3,660,484, but none of these patents discloses that compounds having an α,α-dimethylbenzylurea structure, which is a characteristic chemical structure of the compounds of this invention, are useful as herbicides. *Chemical Abstracts*, 43, 6993i (1949) describes a specific compound, N-(α,αdimethylbenzyl)-N′-phenylurea, but does not teach nor suggest the chemical properties and biological activities of this compound.

Some of the co-inventors of the present invention previously filed U.S. patent applications, i.e., U.S. patent application Ser. Nos. 597,137 filed on July 18, 1975 and 518,812 filed on Oct. 29, 1974 (now patented as U.S. Pat. No. 3,972,909, issued on Aug. 3, 1976), both relating to α, α-dimethylbenzylureas and their applications as herbicides, and they also reported the same α, α-dimethylbenzylureas and their activities in "Selective Control of Cyperaceous Weeds with K-223", *Weed Science*, 23, pp. 18-19, Jan. 1975, but these compounds differ from the compounds of this invention in the type of substituents, such as halogen atoms, attached to the phenyl moiety of the α, α-dimethylbenzyl group.

SUMMARY OF THE INVENTION

According to the present invention there is provided substituted 3-(α, α-dimethylbenzyl)urea compounds of the general formula (I):

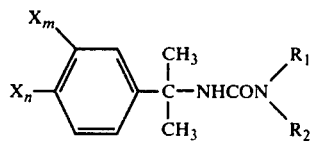

(I)

wherein X is halogen or trifluoromethyl, n and m are 0 or 1, $R_1$ is $C_1$-$C_2$ alkyl or $C_1$-$C_2$ alkoxy and $R_2$ is $C_4$-$C_5$ alkyl, cyclohexyl or phenyl, herbicidal compositions containing the substituted 3-(α, α-dimethylbenzyl)urea compounds as active ingredients, and a method for controlling weed growth employing the compounds and compositions.

DETAILED DESCRIPTION OF THE INVENTION

As an extensive study on the relationship between the chemical structure of α, α-dimethylbenzylureas and their herbicidal activities, particularly against purple nutsedge which was previously difficult to eradicate, it was found that there is a close correlation between the type of substituents on the phenyl moiety and on the nitrogen atom of the urea moiety, the positions at which these substituents are attached, the number of carbon atoms in the alkyl moiety of the aralkyl group, and the like, as set forth below.

(a) The herbicidal activities tend to increase as the number of carbon atoms in the alkyl moiety of the aralkyl group decreases, but compounds wherein the aryl (phenyl) group is attached directly to the nitrogen atom of the urea moiety do not exhibit herbicidal activity.

(b) The compounds having alkyl substituent(s) at the α-position of the alkyl moiety of the aralkyl group exhibit a certain degree of herbicidal activity, but better activity is realized as the number of carbon atoms in the alkyl substituent(s) decreases. Substantially no activity is observed when the phenyl group is replaced by alkyl groups or cycloalkyl groups. Thus, α, α-dimethylbenzyl compounds exhibit the most significant herbicidal activities.

(c) The herbicidal activity decreases or diminishes when the urea moiety is replaced by a thiourea moiety. Thus, the compounds having the basic structure

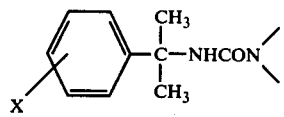

exhibit more or less herbicidal activities.

(d) The substitution of a halogen atom or a trifluoromethyl group on the aryl moiety increases the herbicidal activity. Such increase is particularly significant where the substitution is at the meta-position. Substitution at the para-position or disubstitution at the 3,4-positions is also effective although the degree of activity is less than that of meta-substitution. Ortho-substitution or 2,4-disubstitution does not contribute to an increase in herbicidal activity although the herbicidal activity of compounds having 2,5- or 3,5-substituents has not yet been confirmed. The substitution of substituents other than a halogen atom or a trifluoromethyl group rather decreases the herbicidal activity, although activity has been confirmed with limited types of substituents.

(e) In the group

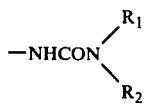

of the compounds of this invention having the formula (I), the group $R_1$ is preferably an alkyl group or an alkoxy group. Of these substituents for $R_1$, better results are realized as the number of carbon atoms in the substituent decreases, but only poor herbicidal activity is obtained when $R_1$ is a hydrogen atom.

For the substituent R$_2$, a specific range of molecular bulkiness is required to retain excellent herbicidal activity. The activity tends to decrease when the alkyl group contains less than 3 or more than 6 carbon atoms. The compounds having a substituted phenyl group for the substituent R$_2$ also exhibit herbicidal activity which is lower than that of those where R$_2$ is a phenyl group.

The compounds of the general formula (I) can be prepared by any known method for manufacturing urea derivatives. For example, they may be prepared by reacting an isocyanate of the general formula (II):

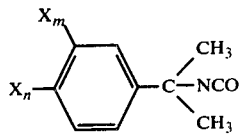

wherein X, n and m have the same meaning as described above for the general formula (I), with an amine of the general formula (III):

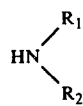

wherein R$_1$ and R$_2$ have the same meaning as described above for the general formula (I). The reaction may be carried out without any solvent or in an appropriate solvent. Any solvents, both polar and non-polar, may be used, although aprotic ones with no active hydrogen atoms are preferred in view of the stability of the isocyanate reactant. Preferred solvents are benzene, toluene, xylene, chlorobenzene, aliphatic hydrocarbons, dichloromethane, chloroform, carbon tetrachloride, acetone, methyl isobutyl ketone, acetonitrile, diethyl ether, and/or ethyl acetate. Selection of a suitable solvent will be made, in practice, on the basis of the solubility of the amine reactant of the general formula (III), the crystallinity of the resultant product, and so forth. The reaction is usually carried out within a temperature range of about 10 to about 120° C. for from several minutes to about 12 hours. With secondary aromatic amines, the reaction is usually effected at about 60 to about 120° C. for about 2 to about 4 hours. In general, the use of primary aliphatic amines will give products with good crystallinity while the use of secondary aliphatic amines will give products with lower crystallinity, although showing higher reactivity.

The compounds of the general formula (I) wherein R$_1$ is alkoxy and R$_2$ is alkyl, cyclohexyl or phenyl may also be prepared by reacting an isocyanate of the general formula (II) with an N-phenylhydroxylamine (or its salt) of the general formula (IV):

R$_2$—NHOH  (IV)

wherein R$_2$ has the same meaning as described above. The resulting N-hydroxy urea of the general formula (V):

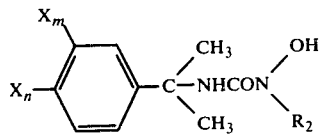

wherein X, n and m have the same meaning as described above for the general formula (I) and R$_2$ has the same meaning as described above is then reacted with a sodium alcoholate, e.g., sodium ethoxide, in ethanol and finally with an alkyl halide, e.g., an alkyl chloride, bromide or iodide, to give the desired product. The final reaction may be carried out by heating the reactants to about 30 to about 80° C. Instead of the compound of the general formula (IV) above, a salt thereof, e.g., R$_2$NHOH·HCl, can also be used.

The isocyanate of the general formula (II), one of the starting materials, may be also prepared by any known method. For example, a carboxylic acid of the general formula (VI):

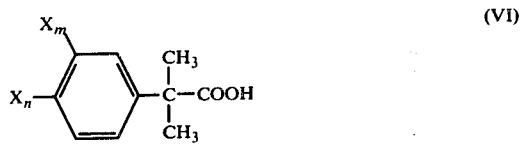

wherein X, n and m have the same meaning as described above for the general formula (I), is reacted, in a known manner, with thionyl chloride to give the corresponding acid chloride. The acid chloride is then subjected to a Curtius rearrangement to give the desired isocyanate of the general formula (II). This reaction may be carried out, for example, by adding an aqueous solution of sodium azide to a solution of the acid chloride in a solvent, e.g., acetone. The reaction temperatures range, in general, from about 0 to about 20° C. and the reaction times from about 30 minutes to about 2 hours. To the reaction mixture are added water and an organic solvent, such as benzene. The organic solvent layer is dried over anhydrous sodium sulfate and heated to about 50 to about 80° C. for about 30 minutes to about 2 hours. The resultant reaction mixture containing the desired isocyanate may be directly used in the subsequent reactions.

The carboxylic acid of the general formula (VI) may be prepared, for example, by dimethylating the corresponding benzyl cyanide in a known manner (see, for example, A.C. Cope, T.T. Foster and P.H. Towle, *J. Amer. Chem. Soc.*, 71, 3929 (1949) or L.B. Taranko and R.H. Perry, Jr., *J. Org. Chem.*, 34 226 (1969)) to form the corresponding nitrile. The nitrile can be then hydrolyzed into the corresponding amide in a conventional manner. The hydrolysis of the nitrile into the corresponding amide may be carried out, for example, by heating the nitrile, together with 80% sulfuric acid, at about 80 to about 100° C. for about 2 to about 4 hours. The amide thus obtained can be hydrolyzed further into the corresponding carboxylic acid of the general formula (VI) in a known manner (see, for example, N. Sperber D. Papa, E. Schwenk, *J. Am. Chem. Soc.*, 70 3091 (1948)) by treating the amide with an excess of an organic nitrite and gaseous hydrogen chloride.

The compounds of the general formula (I) may also be prepared in a known manner according to the following reaction schemes:

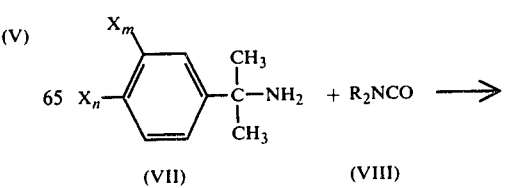

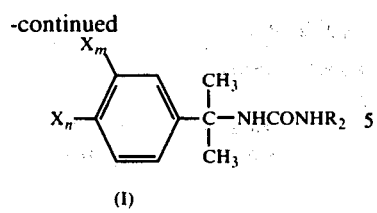

(I)

or

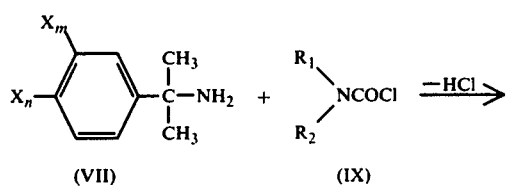

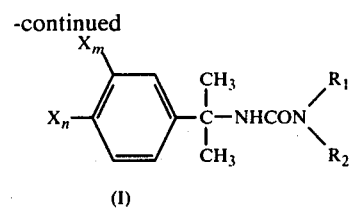

(I)

Typical examples of the compounds of this invention are shown in Table 1 below. The compounds exemplified in the table are designated by a series of code numbers. Hereinafter, the compounds will be identified by these code numbers.

In Table 1, the melting points were determined on a Koffler hot-bench, the nmr spectra were obtained using 60 MHz in $CDCl_3$ or $CCl_4$ with TMS (tetramethylsilane) as an internal standard. The symbols s, d, t, q, m, br, and J stand for singlet, doublet, triplet, quartet, multiplet, broad peak and spin-spin coupling constant, respectively.

TABLE 1

| Compound Number | Chemical Structure | Melting Point (°C) | Refractive Index | NMR δ-Value 60-MHz |
|---|---|---|---|---|
| 1 | 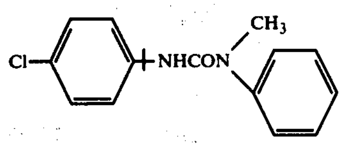 | MP 70–1° | — | NMR ($CDCl_3$) 1.51 (6 H.s.), 3.13 (3 H.s.) 4.63 (1 H.s.), 7.2–7.5 (9 H.m.) |
| 2 | 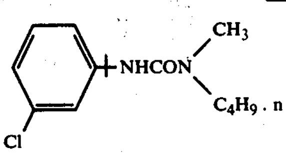 | MP 90–2° | — | NMR ($CDCl_3$) 0.91 (3 H.t. J=7 H.z.), 1.0–1.7 (4 H.m.), 1.62 (6 H.s.), 2.83 (3 H.s.), 3.17 (2 H.q. J=7 H.z.), 4.64 (1.H.s.), 7.1–7.4 (4 H.m.) |
| 3 | 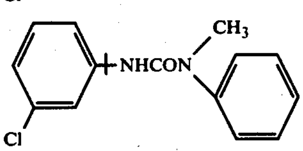 | MP 63–4° | — | NMR ($CCl_4$) 1.49 (6 H.s.), 3.08 (3 H.s.) 4.44 (1 H.s.), 7.0–7.65 (9 H.m.) |
| 4 | 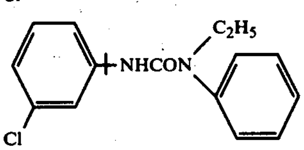 | — | $n_D^{26}$ 1.5588 | NMR ($CCl_4$) 1.04 (3 H.t. J=7 H.z.), 1.49 (6 H.s.), 3.57 (2 H.q. J=7 H.z.), 4.26 (1 H.s.), 7.0–7.5 (9 H.m.) |
| 5 | 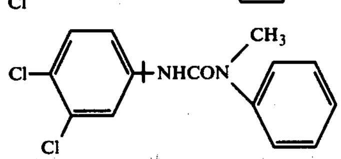 | MP 82–3° | — | NMR ($CDCl_3$) 1.50 (6 H.s.), 3.14 (3 H.s.), 4.60 (1 H.s.), 7.2–7.5 (8 H.m.) |
| 6 | 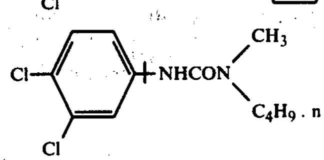 | MP 67–68° | — | — |
| 7 | 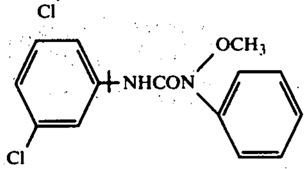 | MP 77° | — | NMR ($CCl_4$) 1.64 (6 H.s.), 3.65 (3 H.s.), 6.18 (1 H.s.), 6.8–7.5 (9 H.m.) |

TABLE 1-continued

| Compound Number | Chemical Structure | Melting Point (°C) | Refractive Index | NMR δ-Value 60-MHz |
|---|---|---|---|---|
| 8 | 3-Br-C6H4-NHCON(CH3)(C6H5) | MP 70° | — | NMR (CDCl3) 1.53 (6 H.s.), 3.18 (3 H.s.), 4.64 (1 H.s.), 7.1–7.5 (9 H.m.) |
| 9 | 4-Br-C6H4-NHCON(CH3)(C6H5) | MP 84° | — | — |
| 10 | 3-Cl-C6H4-NHCON(CH3)(cyclohexyl-H) | MP 138–9° | — | NMR (CDCl3), 1.0–1.9 (10 H.m.), 1.62 (6 H.s.), 2.70 (3 H.s.), 3.90 (1 H.br.), 4.64 (1 H.s.), 7.05–7.35 (4 H.m.) |
| 11 | 3,4-Cl2-C6H3-NHCON(OCH3)(C6H5) | — | $n_D^{27}$ 1.5940 | NMR (CDCl3) 1.66 (6 H.s.), 3.71 (3 H.s.), 6.32 (1 H.s.), 7.0–7.6 (8 H.m.) |
| 12 | 3-CF3-C6H4-NHCON(CH3)(C6H5) | MP 67° | — | NMR (CCl4) 1.54 (6 H.s.), 3.12 (3H.s.), 4.53 (1 H.s.), 7.1–7.5 (9 H.m.) |
| 13 | 3-CF3-C6H4-NHCON(CH3)(n-C4H9) | MP 88° | — | NMR (CCl4) 0.92 (3 H.t. J=7 H.z.), 1.60 (6 H.s.), 1.0–1.7 (4 H.m.), 2.78 (3 H.s.), 3.13 (2 H.q. J=7 H.z.), 4.67 (1 H.s.), 7.3–7.6 (4 H.m.) |
| 14 | 4-Br-C6H4-NHCON(CH3)(cyclohexyl-H) | MP 148° | — | NMR (CDCl3) 1.1–1.8 (10 H.m.), 1.62 (6 H.s.), 2.73 (3 H.s.), 3.90 (1 H.br.), 4.67 (1 H.s.), 7.1–7.5 (4 H.m.) |
| 15 | 4-F-C6H4-NHCON(C2H5)(cyclohexyl-H) | MP 100° | — | NMR (CDCl3) 1.19 (3 H.t. J=7 H.z.) 1.2–1.9 (10 H.m.), 3.19 (2 H.q. J=7 H.z.), 4.03 (1 H.br.) 4.64 (1 H.s.), 6.9–7.5 (4 H.m.) |
| 16 | 3-CF3-C6H4-NHCON(C2H5)(cyclohexyl-H) | MP 94° | — | — |
| 17 | 4-Cl-C6H4-NHCON(C2H5)(C6H5) | — | $n_D^{24}$ 1.5613 | NMR (CCl4) 1.02 (3 H.t. J=7 H.z.), 1.48 (6 H.s.), 3.59 (2 H.q. J=7 H.z.), 4.34 (1 H.s.), 7.2–7.4 (4 H.m.), 7.16 (4.H.s.) |
| 18 | 3-Cl-C6H4-NHCON(CH3)(i-C4H9) | MP 85–6° | — | NMR (CCl4) 0.86 (6 H.d. J=7 H.z.), 1.3–1.7 (1 H.m.), 1.57 (6 H.s.), 2.79 (3 H.s.), 2.98 (2 H.d. J=7 H.z.), 4.70 (1 H.s.), 7.0–7.33 (4 H.m.) |

TABLE 1-continued

| Compound Number | Chemical Structure | Melting Point (°C) | Refractive Index | NMR δ-Value 60-MHz |
|---|---|---|---|---|
| 19 | 3-Cl-C6H4-NHCON(CH3)(C5H11-n) | MP 80° | — | NMR (CCl4) 0.92 (3 H.t. J=7 H.z.), 1.1–1.6 (6 H.m.), 1.61 (6 H.s.), 2.84 (3 H.s.), 3.19 (2 H.t. J=7 H.z.), 4.58 (1 H.s.), 7.2–7.4 (4 H.m.) |
| 20 | 3-Cl-C6H4-NHCON(CH3)(C5H11-i) | MP 112–3° | — | NMR (CCl4) 0.94 (6H.d. J=7 H.z.), 1.1–1.6 (3 H.m.), 1.60 (6 H.s.), 2.81 (3 H.s.), 3.20 (2 H.t. J=7 H.z.), 4.62 (1 H.s.), 7.2–7.4 (4 H.m.) |
| 21 | 3-Cl-C6H4-NHCON(C2H5)(C4H9-n) | MP 85–6° | — | — |
| 22 | 3-Cl-C6H4-NHCON(C2H5)(C4H9-i) | MP 95° | — | NMR (CDCl3) 0.90 (6 H.d. J=7 H.z.), 1.6–2.0 (1 H.m.), 1.63 (6 H.s.), 3.01 (2 H.d. J=7 H.z.), 3.26 (2 H.q. J=7 H.z.), 4.67 (1 H.s.), 7.1–7.4 (4 H.m.) |
| 23 | 4-Cl-C6H4-NHCON(CH3)(C4H9-n) | MP 81° | — | NMR (CCl4) 0.94 (3 H.t. J=7 H.z.), 1.0–1.6 (4 H.m.), 2.78 (3 H.s.), 3.13 (2 H.t. J=7 H.z.), 4.58 (1 H.s.), 7.21 (4 H.m.) |
| 24 | 4-Cl-C6H4-NHCON(CH3)(C4H9-i) | MP 105° | — | — |
| 25 | 4-Cl-C6H4-NHCON(C2H5)(C4H9-n) | MP 63–4° | — | — |
| 26 | 3,4-Cl2-C6H3-NHCON(C2H5)(C6H5) | — | $n_D^{23}$ 1.5632 | NMR (CDCl3) 1.02 (3 H.t. J=7 H.z.), 1.48 (6 H.s.), 3.63 (2 H.q. J=7 H.z.), 4.46 (1 H.s.), 7.0–7.6 (8 H.m.) |
| 27 | 3-Br-C6H4-NHCON(C2H5)(C6H5) | MP 67° | — | NMR (CDCl3) 1.04 (3 H.t. J=7 H.z.), 1.50 (6 H.s.), 3.65 (2 H.q. J=7 H.z.), 4.06 (1 H.s.), 7.1–7.6 (9 H.m.) |
| 28 | 3-Cl-C6H4-NHCON(OC2H5)(C6H5) | MP 71° | — | NMR (CCl4) 1.28 (3 H.t. J=7 H.z.), 1.64 (6 H.s.), 3.87 (2 H.q. J=7 H.z.), 6.16 (1 H.s.), 6.8–7.5 (9 H.m.) |
| 29 | 4-Cl-C6H4-NHCON(OCH3)(C6H5) | MP 91–2° | — | NMR (CDCl3) 1.71 (6 H.s.), 3.74 (3 H.s.), 6.33 (1 H.s.), 7.1–7.6 (9 H.m.) |
| 30 | 4-Cl-C6H4-NHCON(OC2H5)(C6H5) | MP 65° | — | NMR (CDCl3) 1.34 ( H.t. J=7 H.z.), 1.73 (6 H.s.), 3.95 (2 H.q. J=7 H.z.), 6.36 (1 H.s.), 7.1–7.6 (9 H.m.) |

TABLE 1-continued

| Compound Number | Chemical Structure | Melting Point (° C.) | Refractive Index | NMR δ-Value 60-MHz |
|---|---|---|---|---|
| 31 | 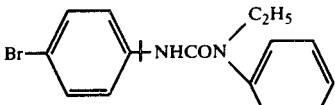 | — | $n_D^{25}$ 1.5708 | NMR (CCl$_4$) 1.01 (3 H.t. J=7 H.z.), 1.48 (6 H.s.), 3.58 (2 H.q. J=7 H.z.), 4.28 (1 H.s.), 7.0–7.6 (9 H.m.) |
| 32 | 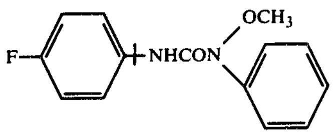 | MP 65° | — | NMR (CDCl$_3$) 1.70 (6 H.s.), 3.72 (3 H.s.), 6.28 (1 H.s.), 6.9–7.6 (9 H.m.) |
| 33 | 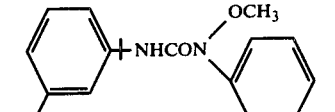 | MP 85° | — | NMR (CDCl$_3$) 1.64 (6 H.s.), 3.75 (3 H.s.), 6.38 (1 H.s.), 7.0–7.7 (9 H.m.) |
| 34 | 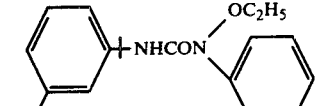 | MP 61 | — | NMR (CDCl$_3$) 1.35 (3 H.t. J=7 H.z.), 1.75 (6 H.s.), 3.97 (2 H.q. J=7 H.z.), 6.41 (1 H.s.), 7.0–7.7 (9 H.m.) |
| 35 | 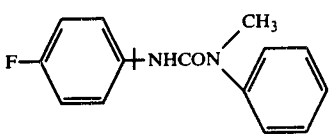 | — | $n_D^{24}$ 1.5443 (purity 90%) | NMR (CCl$_4$) 1.52 (6 H.s.), 3.13 (3 H.s.), 4.47 (1 H.s.) 6.9–7.4 (9 H.m.) |
| 36 | 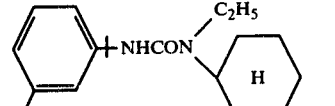 | MP 119° | — | — |
| 37 | 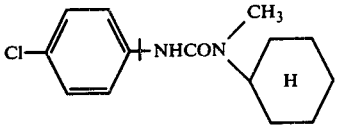 | MP 149–150° | — | NMR (CDCl$_3$) 1.0–1.9 (10 H.m.), 1.64 (6 H.s.), 2.74 (3 H.s.), 3.95 (1 H.br.), 4.64 (1 H.s.), 7.27 (4 H.s.) |
| 38 | 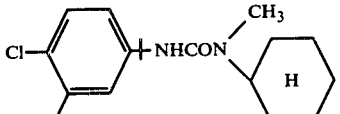 | MP 118–9° | — | — |
| 39 | 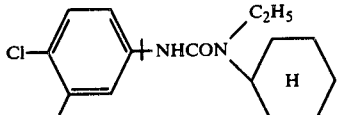 | MP 109° | — | — |
| 40 | 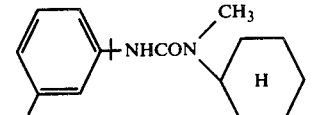 | MP 146° | — | NMR (CDCl$_3$) 0.9–1.9 (10 H.m.), 1.65 (6 H.s.), 2.76 (3 H.s.), 3.9 (1 H.br.), 4.65 (1 H.s.), 7.05–7.5 (4 H.m.) |
| 41 | 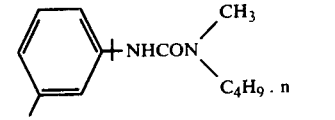 | MP 102° | — | NMR (CDCl$_3$) 0.93 (3 H.t. J=7 H.z.), 1.64 (6 H.s.), 1.0–1.7 (4 H.m.), 2.87 (3 H.s.), 3.21 (2 H.t. J=7 H.z.), 4.65 (1 H.s.), 7.1–7.5 (4 H.m.) |

TABLE 1-continued

| Compound Number | Chemical Structure | Melting Point (°C) | Refractive Index | NMR δ-Value 60-MHz |
|---|---|---|---|---|
| 42 | 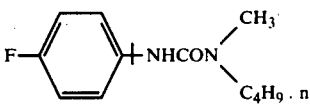 | MP 65° | — | NMR (CCl₄) 0.91 (3 H.t. J=7 H.z.), 1.57 (6 H.s.), 2.75 (3 H.s.), 3.12 (2 H.q. J=7 H.z.), 1.1–1.7 (4 H.m.), 4.61 (1 H.s.), 6.7–7.4 (4 H.m.) |

Note: The designation "$+$" means $-\underset{\underset{CH_3}{|}}{\overset{\overset{CH_3}{|}}{C}}-$.

The following specific examples are given to illustrate the method for preparing the compounds of the invention. Unless otherwise indicated herein, all parts, percents, ratios and the like are by weight.

SYNTHESIS EXAMPLE 1

3-(m-Chloro-α,α-dimethylbenzyl)-1-methyl-1-phenylurea 140 g of potassium hydroxide was added incrementally, with vigorous stirring, to a solution of 142 g of m-chlorobenzyl cyanide and 400 g of methyl iodide in 600 ml of dimethyl sulfoxide at a temperature of from 30° to 40° C. over a period of 2 hours. After the addition the mixture was heated to 60° to 70° C. and kept at that temperature for 3 hours. To the resultant reaction mixture was added benzene and water. The benzene layer was separated and washed with a 2N aqueous sodium hydroxide solution and then water, and dried over sodium sulfate. The dried benzene layer was concentrated by evaporating off the solvent and the residue distilled under reduced pressure, to obtain 149 g of m-chloro-α,α-dimethylbenzyl cyanide as a colorless liquid having a boiling point of 75°-80° C./0.4 mmHg.

127 g of the thus obtained nitrile was added to 150 ml of 80% sulfuric acid and the mixture heated with stirring to 95° to 100° C. for 2 hours. The hot reaction mixture was poured into 1 l of water. The thus precipitated crystals were filtered off, washed with water and then hexane, and recrystallized from a mixture of benzene and ethanol to obtain 131 g of 2-(m-chlorophenyl)-2-methylpropionamide as white crystals.

94 g of this product was dissolved in 400 ml of acetic acid, and anhydrous hydrogen chloride was passed through the resulting solution at room temperature (about 20°-30° C.) for 30 minutes. 77 g of n-butyl nitrite was then added dropwise to the solution with stirring over a period of 2 hours. After the dropwise addition, the mixture was heated under reflux for 8 hours and then the solvent was evaporated off under reduced pressure. The residue was dissolved in benzene and extracted with 2N sodium hydroxide. The extract was rendered acidic with 2N hydrochloric acid. The thus precipitated crystals were filtered off. The crude crystals were recrystallized from a mixture of benzene and n-hexane to obtain 82 g of 2-(m-chlorophenyl)-2-methylpropionic acid as white crystals.

To 80 g of the thus obtained product were added 100 ml of benzene and 100 g of thionyl chloride. The mixture was heated under reflux for 2 hours. The benzene and excess thionyl chloride were then evaporated off to obtain 94 g of 2-(m-chlorophenyl)-2-methylpropionyl chloride as a colorless liquid. To a solution of 2.2 g of the resultant acid chloride in 5 ml of acetone was added dropwise, with stirring, 0.7 g of sodium azide in 5 ml of water over a period of 15 minutes, while keeping the mixture at a temperature of 10° C. throughout the addition. The reaction was continued for an additional 30 minutes. The reaction mixture was extracted with benzene and the benzene extract dried over sodium sulfate and heated to 60° C. for an hour. After cooling, the resultant solution of m-chloro-α,α-dimethylbenzyl isocyanate was added to 1.1 g of N-methylaniline and the mixture heated under reflux for 3 hours. After cooling, the reaction mixtutre was washed with 2N sodium hydroxide, 2N hydrochloric acid and water in that order, and dried over sodium sulfate. The solvent was then evaporated off to obtain crystals, which were recrystallized from n-hexane to give 2.3 g of the title compound as white crystals.

SYNTHESIS EXAMPLE 2

1-n-Butyl-3-(m-chloro-α,α-dimethylbenzyl)-1-methylurea 3.9 g of m-chloro-α,α-dimethylbenzyl isocyanate prepared from the corresponding cyanide in the same way as in Synthesis Example 1, was added to a solution of 1.8 g of N-n-butyl-N-methylamine in 20 ml of benzene and the mixture vigorously stirred. After allowing the mixture to stand overnight, the reaction solution was washed with a 2N aqueous hydrochloric acid solution, a 2N aqueous sodium hydroxide solution and water in that order, and the organic layer was dried over sodium sulfate. The layer was concentrated by evaporating off the solvent to obtain crystals, which were recrystallized from n-hexane to obtain 5.0 g of the title compound as crystals.

SYNTHESIS EXAMPLE 3

3-(m-Chloro-α,α-dimethylbenzyl)-1-cyclohexyl-1-methylurea

A solution of 1.2 g of N-methyl-N-cyclohexylamine in 5 ml of n-hexane was added to a solution of 0.01 mole of m-chloro-α,α-dimethylbenzyl isocyanate (prepared from the corresponding cyanide in the same way as shown in Synthesis Example 1) in 10 ml of benzene. The mixture was kept at room temperature for 6 hours and concentrated under reduced pressure to obtain crystals, which were recrystallized from n-hexane to give 2.8 g of the title compound as white crystals.

SYNTHESIS EXAMPLE 4

3-(3,4-Dichloro-α,α-dimethylbenzyl)-1-methyl-1-phenylurea 4.6 g of 3,4-dichloro-α,α-dimethylbenzyl isocyanate, prepared from the corresponding cyanide in the same way as in Synthesis Example 1, was added to a solution of 2.2 g of N-methylaniline in 20 ml of benzene and the mixture was heated under reflux for 2 hours. After allowing the mixture to stand overnight, the reaction solution was washed with a 2N aqueous hydrochloric acid solution, a 2N aqueous sodium hydroxide solution and water in that order, and the organic layer was dried over sodium sulfate. The layer was concentrated by evaporating off the solvent to obtain crystals, which were recrystallized from n-hexane to obtain 5.8 g of the title compound as crystals.

SYNTHESIS EXAMPLE 5

3-(m-Chloro-α,α-dimethylbenzyl)-1-methoxy-1-phenylurea

A solution of 2.2 g of N-phenylhydroxylamine in 10 ml of benzene was added to a solution of 0.02 mole of m-chloro-α,α-dimethylbenzyl isocyanate (prepared from the corresponding cyanide in the same way as in Synthesis Example 1) in 10 ml of benzene. The mixture was stirred well and allowed to stand overnight. The precipitated crystals were filtered off and washed with n-hexane to yield 5.7 g of 3-(m-chloro-α,α-dimethylbenzyl)-1-hydroxy-1-phenylurea. To 3.1 g of the urea was added a solution of 550 mg of sodium methoxide in 10 ml of methanol. The mixture was made homogeneous by stirring and 1.5 g of methyl iodide was added thereto. The mixture was then heated under reflux for 2 hours. The solvent was evaporated off and the residue was extracted with benzene and water was added. The benzene layer was dried over sodium sulfate and the solvent was distilled off to give crystals, which were recrystallized from a mixture of n-hexane and benzene to obtain 2.7 g of the title compound.

SYNTHESIS EXAMPLE 6

3-(m-Chloro-α,α-dimethylbenzyl)-1-methyl-1-pentylurea

A solution of 3.9 g of m-chloro-α,α-dimethylbenzyl isocyanate, prepared from the corresponding cyanide in the same way as in Synthesis Example 1, in 10 ml of n-hexane was added to 4 g of N-methyl-N-pentylamine and the mixture was allowed to stand overnight. The precipitated crystals were separated by filtration and washed thoroughly with n-hexane to obtain 5.4 g of the title compound.

SYNTHESIS EXAMPLE 7

1-i-Butyl-3-(p-chloro-α,α-dimethylbenzyl)-1-methylurea 3.9 g of p-chloro-α,α-dimethylbenzyl isocyanate, prepared from the corresponding cyanide in the same way as in Synthesis Example 1, was added to 1.9 g of N-i-butyl-N-methylamine. The precipitated crystals were separated by filtration and recrystallized from n-hexane to obtain 5.2 g of the title compound.

SYNTHESIS EXAMPLE 8

1-n-Butyl-3-(p-chloro-α,α-dimethylbenzyl)-1-ethylurea

A solution of 3.9 g of p-chloro-α,α-dimethylbenzyl isocyanate, prepared from the corresponding cyanide in the same way as in Synthesis Example 1, in 20 ml of methyl isobutyl ketone was added to 2.2 g of N-n-butylethylamine. The solvent was then removed by distillation under reduced pressure and the resulting crystals were recrystallized from n-hexane to obtain 5.1 g of the title compound.

SYNTHESIS EXAMPLE 9

3-(p-Chloro-α,α-dimethylbenzyl)-1-ethyl-1-phenylurea

A solution of 3.9 g of p-chloro-α,α-dimethylbenzyl isocyanate, prepared from the corresponding cyanide in the same way as in Synthesis Example 1, in 20 ml of toluene was added to 2.7 g of N-ethylaniline and the mixture was heated under reflux for 3 hours. After allowing the reaction mixture to cool, the mixture was washed successively with 2N hydrochloric acid, 2N aqueous sodium hydroxide and water. The organic layer was dried over anhydrous sulfate and the solvent was removed by distillation under reduced pressure to obtain 6.2 g of the title compound as a light brown oily substance.

SYNTHESIS EXAMPLE 10

3-(p-Chloro-α,α-dimethylbenzyl)-1-ethoxy-1-phenylurea

A solution of 19.6 g of p-chloro-α,α-dimethylbenzyl isocyanate, prepared from the corresponding cyanide in the same way as in Synthesis Example 1, in 10 ml of diethyl ether was added dropwise to a solution of 10.9 g of N-phenylhydroxylamine in 10 ml of diethyl ether. After completion of the addition, the mixture was stirred for 30 minutes whereby 3-(p-chloro-α,α-dimethylbenzyl)-1-hydroxy-1-phenylurea precipitated. The resulting crystals were separated by filtration and dried. A 3.0 g portion of the crystals thus obtained was added to 10 ml of an ethanolic solution of 750 mg of sodium ethoxide, and, after the crystals had been completely dissolved, 1.2 g of ethyl bromide was added thereto followed by heating at 60° C. for 2 hours. The solvent was then removed by distillation under reduced pressure, and the resulting residue was extracted with water and benzene. The benzene layer was washed successively with 2N aqueous sodium hydroxide and water and dried over anhydrous sodium sulfate. The solvent was removed by distillation to precipitate crystals which were then recrystallized from a mixture of benzene and hexane to obtain 3.1 g of the title compound as white crystals.

SYNTHESIS EXAMPLE 11

3-(3,4-Dichloro-α,α-dimethylbenzyl)-1-cyclohexyl-1-ethylurea

A solution of 2.3 g of 3,4-dichloro-α,α-dimethylbenzyl isocyanate, prepared from the corresponding cyanide in the same way as in Synthesis Example 1, in 10 ml of chloroform was added to 1.5 g of N-ethylcyclohexylamine. The solvent was then removed by distillation and the resulting white crystals were recrystallized from a mixture of benzene-n-hexane to obtain 2.6 g of the title compound.

SYNTHESIS EXAMPLE 12

3-(m-Trifluoromethyl-α,α-dimethylbenzyl)-1-methyl-1-phenylurea

A solution of 2.3 g of m-trifluoromethyl-α,α-dimethylbenzyl isocyanate in 5 ml of benzene was added to 1.1 g of N-methylaniline in 5 ml of benzene and the mixture was heated under reflux for 2 hours. After allowing the reaction mixture to cool, the mixture was washed successively with 2N aqueous sodium hydroxide, 2N hydrochloric acid and water and dried over anhydrous sodium sulfate. The solvent was then removed by distillation and the resulting crystals were recrystallized from n-hexane to obtain 2.6 g of the title compound.

SYNTHESIS EXAMPLE 13

3-(m-Trifluoromethyl-α,α-dimethylbenzyl)-1-methoxy-1-phenylurea

A solution of 2.2 g of m-trifluoromethyl-α,α-dimethylbenzyl isocyanate in 10 ml of dichloromethane was added dropwise to a solution of 1.1 g of N-phenylhydroxylamine in 10 ml of dichloromethane over a period of 10 minutes. After completion of the addition, the mixture was stirred for 30 minutes and the solvent was removed by distillation. The resulting white crystals were dried well and dissolved in 10 ml of a methanolic solution of 600 mg of sodium methoxide. 2.0 g of methyl iodide was added to the solution and the mixture was heated under reflux for 2 hours. The reaction mixture was concentrated and extracted with water and benzene. The benzene layer was washed successively with 2N aqueous sodium hydroxide and water and dried over anhydrous sodium sulfate. The solvent was removed by distillation and the resulting crystals were then recrystallized from a mixture of benzene and hexane to obtain 2.4 g of the title compound.

SYNTHESIS EXAMPLE 14

1-Cyclohexyl-1-ethyl-3-(p-fluoro-α,α-dimethylbenzyl-)urea

A solution of 1.8 g of p-fluoro-α,α-dimethylbenzyl isocyanate in 20 ml of n-hexane was added to 1.4 g of N-ethylcyclohexylamine, and the mixture was allowed to stand overnight. The solvent was then removed by distillation and the resulting crystals were washed with cold n-pentane to obtain 2.7 g of the title compound.

SYNTHESIS EXAMPLE 15

3-(m-Bromo-α,α-dimethylbenzyl)-1-methyl-1-phenylurea 2.4 g of m-bromo-α,α-dimethylbenzyl isocyanate, prepared from the corresponding cyanide in the same way as in Synthesis Example 1, was added to 1.1 g of N-methylaniline and the mixture was heated at 60° C. for 2 hours. After allowing the reaction mixture to cool, the precipitated white crystals were separated by filtration and washed with n-hexane to obtain 3.0 g of the title compound.

We have now found that certain urea compounds of the structure wherein an aryl group is attached via the tertiary carbon atom of the isopropyl group to the amino nitrogen atom of the urea skeleton, are useful as selective herbicides. The structure of the urea compounds according to the present invention is unique and definitely distinguished from that of the prior art urea herbicides.

The compounds of the general formula (I) have outstandingly high selective phytotoxicity. Thus, they can control a wide range of weeds without being phytotoxic to certain useful plants. For example, they can control weeds belonging to Gramineae Fm. such as meadow foxtail (Alopecurus sp.), barnyard grass (Echinochloa sp.), crabgrass (Digitaria sp.), bluegrass (Poa sp.), green foxtail (Setaria sp.), oats (Avena sp.), goose grass (Eleusine sp.), and Johnson grass (Sorghum sp.), broadleaved weeds such as lambsquaters (Chenopodium sp.), pigweed (Amaranthus sp.), chickweed (Stellaria sp.), false pimpernel (Lindernia sp.), monochoria (Monochoria sp.), common rag weed (Ambrosia sp.), common purslane or pussley (Portulaca sp.), annual fleabane (Erigeron sp.), smartweed (Polygonum sp.), and toothcup (Rotala sp.), and Cyperaceae Fm. such as purple nutsedge, umbrella plant, or flatsedge (Cyperus sp.), slender spikerush (Eleocharis sp.), bulrush or three square grass (Scirpusa sp.), and green Kyllinga (Kyllinga sp.). Those weeds belonging to Cyperaceae are so persistent and prolific that they are very hard to eradicate. Propagation by tubers is a major means of spreading in cultivated areas. Control of these weeds by known urea type herbicides, such as fenuron, monuron, diuron, or linuron, is only partially effective, and the tubers retain a capacity for repeated regrowth after shoots or foliar parts of the plants are affected by the chemicals. The herbicidal action of the compounds of the present invention is especially outstanding on those weeds belonging to Cyperaceae Fm. as well as other noxious weeds which have previously been difficult to control.

The compounds of the general formula (I) are practically non-phytotoxic to many useful crops such as rice, barley, wheat, soybean, peanut, corn, beet, cotton, tomato, melon, potato, sweet potato, radish, carrot, cabbage, onion, turf, sugarcane, tobacco, sunflower, strawberry, rapeseed, eggplant, tea, fruit trees, woody plants, and pasturage.

Due to their high selectivity, the compounds can be used in controlling weeds in the above stated crop fields preferably by a pre-emergence treatment or by a pre-plant soil-incorporation treatment.

Referring now to the structural activity relationship of the compounds of the present invention, we found that basic skeleton

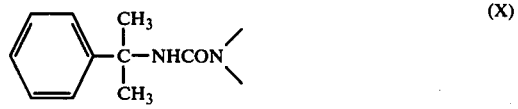 (X)

is essential to selective herbicidal activity. Thus, only a slight change, as of the isopropylidene group into a methylene, ethylene or ethylidene group or of the urea group into a thiourea group significantly reduces the selectivity and/or the phytotoxicity. Further, in detail, compounds possessing the foregoing basic skeleton are generally more or less phytotoxic. Introduction of one or two halogen or trifluoromethyl substituents into the m- or p- position (or both) of the aromatic ring, however, causes great enhancement of herbicidal activity. While introduction of other groups into the aromatic ring reduces herbicidal activity.

The $R_1$ group in the general formula (I) plays an important role in activity, thus introduction of a lower alkoxy, or lower alkyl group increases activity, while replacement of the $R_1$ group with a hydrogen atom reduces activity. An important aspect of herbicidal activity is the molecular bulkiness of the $R_2$ group in the general formula (I). Activity is maximized when the number of carbon atoms in the $R_2$ moiety is from 4 to 6, thus maximum phytotoxicity can be attained when $R_2$ is one of butyl, amyl, cyclohexyl, or phenyl.

The compounds of the above-described general formula (I) may be formulated into various compositions. That is, the compounds may be formulated into any known formulations such as dusts, granules, emulsifiable concentrates, wettable powders and pastes, by use of inert solid carriers such as clay, kaolin, diatomaceous earth, calcium silicate and talc, liquid media such as water, methanol, benzene, toluene, xylene, methylnaphthalene, methyl Cellosolve and chlorobenzene or wetting agents, dispersants and emulsifiers. Further, the herbicidal compositions of the present invention may be used together with or in admixture with fertilizers, soil improvers, insecticides, fungicides, other herbicides or plant growth regulators.

Procedures for the preparation of the present herbicidal compositions are illustrated with reference to the following Examples.

EXAMPLE 1

A mixture comprising 50 parts by weight of Compound 1, 50 parts by weight of bentonite and 5 parts by weight of polyoxyethylene alkylaryl ether is thoroughly pulverized to obtain a wettable powder containing 50% of the active ingredient compound.

EXAMPLE 2

A mixture comprising 10 parts by weight of Compound 16, 15 parts by weight of bentonite, 73 parts by weight of clay and 2 parts by weight of sodium dodecylbenzenesulfonate is thoroughly kneaded with about 25 parts by weight of water, granulated and then dried to obtain granules containing 10% of the active ingredient.

EXAMPLE 3

A mixture comprising 50 parts by weight of Compound 22, 45 parts by weight of bentonite and 5 parts by weight of polyoxyethylene alkylaryl ether is thoroughly pulverized to obtain a wettable powder containing 50% of the active ingredient.

EXAMPLE 4

A mixture comprising 10 parts by weight of Compound 40, 15 parts by weight of bentonite, 73 parts by weight of clay, and 2 parts by weight of sodium dodecylbenzenesulfonate is thoroughly kneaded with about 25 parts by weight of water, granulated and then dried to obtain granules containing 10% of the active ingredient.

The effects of the present herbicidal compositions are exemplified below with reference to various test examples.

TEST 1

Ceramic pots of 1/8,850 are in size were packed with paddy soil. Seeds of monochoria (*Monochoria vaginalis*) and barnyard grass (*Echinochoa crusgalli*) were mixed with the surface soil. Two sheaves of paddy rice and slender spikerush (*Eleocharis acicularis*) were transplanted into each pot. Each of the pots was watered the following day to the depth of 4 cm to provide paddy conditions. Three days after the transplantation, a wettable powder of each active ingredient of the invention was used, diluted with 1,000 l/ha water, to treat the irrigation water at the dosage of 5 kg/ha. As a reference herbicide, diuron [3-(3,4-dichloro-phenyl)-1,1-dimethylurea] was used. The test was conducted in a greenhouse. After 21 days, the herbicidal effects and phytotoxicity to paddy rice were observed and rated by grades 0 (no damage) to 10 (complete growth inhibition) for slender spikerush and 0 (no injury) to 10 (killed) for the others.

The test results are summarized in Table 2 below. Diuron was used as a herbicidal reference.

TABLE 2

| Compound No. | Herbicidal Effect | | | Phytotoxicity to Paddy Rice |
|---|---|---|---|---|
| | Barnyard Grass | Slender Spikerush | Monochoria | |
| 1 | 10 | 10 | 10 | 5 |
| 2 | 10 | 10 | 10 | 4 |
| 3 | 10 | 10 | 10 | 7 |
| 4 | 10 | 10 | 10 | 6 |
| 5 | 10 | 10 | 10 | 8 |
| 6 | 10 | 9 | 10 | 4 |
| 7 | 10 | 10 | 10 | 8 |
| 8 | 10 | 10 | 10 | 8 |
| 9 | 10 | 10 | 8 | 6 |
| 10 | 10 | 10 | 10 | 5 |
| 11 | 10 | 10 | 10 | 4 |
| 12 | 10 | 10 | 10 | 4 |
| 13 | 10 | 10 | 6 | 6 |
| 14 | 10 | 10 | 10 | 4 |
| 15 | 10 | 10 | 8 | 2 |
| 16 | 10 | 10 | 8 | 0 |
| 17 | 10 | 8 | 10 | 8 |
| 18 | 10 | 10 | 10 | 8 |
| 19 | 10 | 10 | 10 | 2 |
| 20 | 10 | 10 | 10 | 6 |
| 21 | 10 | 10 | 10 | 6 |
| 22 | 10 | 10 | 10 | 2 |
| 23 | 10 | 10 | 10 | 6 |
| 24 | 9 | 8 | 10 | 0 |
| 25 | 10 | 10 | 10 | 2 |
| 26 | 10 | 9 | 10 | 0 |
| 27 | 10 | 10 | 10 | 8 |
| 28 | 10 | 10 | 10 | 8 |
| 29 | 10 | 10 | 10 | 8 |
| 30 | 10 | 10 | 10 | 5 |
| 31 | 10 | 10 | 8 | 0 |
| 32 | 10 | 10 | 8 | 4 |
| 33 | 10 | 10 | 8 | 7 |
| 34 | 10 | 10 | 10 | 4 |
| 35 | 10 | 10 | 8 | 6 |
| 36 | 10 | 10 | 10 | 5 |
| 37 | 10 | 10 | 10 | 2 |
| 38 | 10 | 8 | 10 | 0 |
| 39 | 10 | 8 | 10 | 0 |
| 40 | 10 | 10 | 10 | 6 |
| 41 | 10 | 10 | 10 | 8 |
| 42 | 10 | 10 | 10 | 4 |
| Diuron | 10 | 10 | 10 | 10 |

The results given in Table 2 above demonstrate that the compounds of the present invention possess strong herbicidal activity against different paddy field weeds coupled with low phytotoxicity to paddy rice.

TEST 2

(A) Ceramic pots of 1/8,850 are in size were packed with field soil. Seeds of crabgrass and pigweed were mixed with the surface soil forming the upper 2 cm deep layer. Immediately after, 10 kg/ha A.I. (hereinafter referred to "A.I." as an abbreviation of active ingredient) of a wettable powder of each active ingredient of the invention, diluted with 1,000 l/ha was sprayed over the surface of the soil.

(B) Ceramic pots of 1/8,850 are in size were packed with field soil to the depth of 10 cm. The soil was then removed and sprayed and mixed with 10 kg/ha A.I. of a wettable powder of each active ingredient of the invention, diluted with 1,000 l/ha of water. The so-treated soil was brought back to the pots. Immediately after that, seven tubers of purple nutsedge were planted 3 cm deep in the soil.

Herbicidal effects were observed after 14 days for (A) and after 30 days for (B), and rated by grades 0 (no damage) to 10 (complete damage).

The test results are summarized in Table 3 below. Diuron was used as a reference herbicide.

TABLE 3

| Compound No. | Herbicidal Effect | | |
|---|---|---|---|
| | Crabgrass | Pigweed | Purple Nutsedge |
| 1 | 9 | 8 | 10 |

TABLE 3-continued

| Compound No. | Herbicidal Effect | | |
|---|---|---|---|
| | Crabgrass | Pigweed | Purple Nutsedge |
| 2 | 10 | 9 | 10 |
| 3 | 10 | 10 | 10 |
| 4 | 10 | 6 | 10 |
| 5 | 10 | 4 | 10 |
| 6 | 8 | 6 | 9 |
| 7 | 10 | 10 | 10 |
| 8 | 10 | 6 | 10 |
| 9 | 10 | 4 | 10 |
| 10 | 9 | 4 | 9 |
| 11 | 10 | 4 | 9 |
| 12 | 10 | 6 | 10 |
| 13 | 8 | 7 | 10 |
| 14 | 8 | 8 | 7 |
| 15 | 6 | 6 | 10 |
| 16 | 6 | 4 | 9 |
| 17 | 9 | 8 | 10 |
| 18 | 10 | 4 | 10 |
| 19 | 6 | 6 | 9 |
| 20 | 8 | 6 | 9 |
| 21 | 9 | 8 | 10 |
| 22 | 9 | 8 | 9 |
| 23 | 8 | 4 | 10 |
| 24 | 0 | 4 | 10 |
| 25 | 6 | 4 | 8 |
| 26 | 8 | 4 | 9 |
| 27 | 10 | 6 | 10 |
| 28 | 10 | 8 | 10 |
| 29 | 10 | 6 | 10 |
| 30 | 9 | 5 | 10 |
| 31 | 10 | 6 | 8 |
| 32 | 10 | 8 | 10 |
| 33 | 10 | 6 | 10 |
| 34 | 10 | 6 | 10 |
| 35 | 10 | 8 | 10 |
| 36 | 9 | 4 | 9 |
| 37 | 10 | 4 | 8 |
| 38 | 8 | 2 | 8 |
| 39 | 6 | 2 | 7 |
| 40 | 9 | 2 | 9 |
| 41 | 9 | 6 | 10 |
| 42 | 8 | 6 | 10 |
| Diuron | 10 | 10 | 5 |

These results in Table 3 above show that the compounds of this invention possess strong herbicidal activity against a broad range of field weeds.

TEST 3

Ceramic pots of 1/5,000 are were packed with field soil. The soil from the surface to a depth of 5 cm was removed, and sprayed and mixed well with 5 and 10 kg/ha A.I. of a wettable powder of each active ingredient of the invention, diluted with 1,000 l/ha of water. The soil so treated was returned to the pots. Immediately thereafter, seeds of soybean, peanut, tomato, cotton and maize were sown 2 cm deep in the soil. The phytotoxicity to these crops was determined after 24 days, and rated as follows:

| Phytotoxicity | Index |
|---|---|
| 9% or less damage | 0 |
| 10–19% " | 1 |
| 20–29% " | 2 |
| 30–39% " | 3 |
| 40–49% " | 4 |
| 50–59% " | 5 |
| 60–69% " | 6 |
| 70–79% " | 7 |
| 80–89% " | 8 |
| 90–99% " | 9 |
| 100% (killed) | 10 |

The test results are summarized in Table 4 below. Diuron was used as a reference.

TABLE 4

| Compound No. | Crop | | | | | | | | | |
|---|---|---|---|---|---|---|---|---|---|---|
| | Soybean | | Peanut | | Tomato | | Cotton | | Maize | |
| | 5* | 10 | 5 | 10 | 5 | 10 | 5 | 10 | 5 | 10 |
| 1 | 2 | 6 | 0 | 0 | 0 | 0 | 0 | 0 | 4 | 6 |
| 2 | 2 | 4 | 0 | 0 | 0 | 1 | 0 | 0 | 5 | 6 |
| 3 | 3 | 8 | 0 | 0 | 0 | 1 | 0 | 0 | 6 | 7 |
| 4 | 2 | 6 | 0 | 0 | 0 | 0 | 0 | 0 | 4 | 6 |
| 5 | 1 | 2 | 0 | 0 | 0 | 0 | 0 | 0 | 4 | 6 |
| 6 | 2 | 3 | 0 | 0 | 0 | 0 | 0 | 0 | 4 | 5 |
| 7 | 6 | 7 | 0 | 2 | 0 | 2 | 0 | 0 | 7 | 8 |
| 8 | 3 | 7 | 0 | 0 | 0 | 0 | 0 | 0 | 5 | 7 |
| 9 | 2 | 5 | 0 | 0 | 0 | 0 | 0 | 0 | 3 | 5 |
| 10 | 3 | 7 | 0 | 0 | 0 | 0 | 0 | 0 | 4 | 6 |
| 11 | 2 | 3 | 0 | 0 | 0 | 0 | 0 | 0 | 4 | 6 |
| 12 | | | | | | | | | | |
| 13 | | | | | | | | | | |
| 14 | | | | | | | | | | |
| 15 | | | | | | | | | | |
| 16 | | | | | | | | | | |
| 17 | | | | | | | | | | |
| 18 | | | | | | | | | | |
| 19 | | | | | | | | | | |
| 20 | | | | | | | | | | |
| 21 | | | | | | | | | | |
| 22 | | | | | | | | | | |
| 23 | | | | | | | | | | |
| 24 | | | | | | | | | | |
| 25 | | | | | | | | | | |
| 26 | 0 | 3 | 0 | 0 | 0 | 0 | 0 | 0 | 3 | 4 |
| 27 | | | | | | | | | | |
| 28 | 5 | 6 | 0 | 0 | 0 | 1 | 0 | 0 | 5 | 6 |
| 29 | | | | | | | | | | |
| 30 | | | | | | | | | | |
| 31 | | | | | | | | | | |
| 32 | | | | | | | | | | |
| 33 | | | | | | | | | | |
| 34 | | | | | | | | | | |
| 35 | | | | | | | | | | |
| 36 | 2 | 6 | 0 | 0 | 0 | 0 | 0 | 0 | 3 | 5 |
| 37 | | | | | | | | | | |
| 38 | | | | | | | | | | |
| 39 | | | | | | | | | | |
| 40 | | | | | | | | | | |
| 41 | | | | | | | | | | |
| 42 | | | | | | | | | | |
| Diuron | 5 | 10 | 3 | 6 | 10 | 10 | 0 | 2 | 5 | 9 |

*kg/ha

TEST 4

Ceramic pots of 1/8,850 are in size were packed with paddy soil. Seeds of barnyard grass and monochoria were mixed with the surface soil, and slender spikerush was transplanted. Each of the pots was watered the next day to a depth of 4 cm to provide paddy conditions. Three days after the transplantation, a wettable powder of each active ingredient of the invention was used, after dilution with 1,000 l/ha of water, to treat the irrigation water at a dosage of 1 and 2 kg/ha A.I. Diuron was used as a reference herbicide. After 21 days, the herbicidal effects were observed and rated by grades 0 (no damage) to 10 (complete growth inhibition) for slender spikerush and 0 (no injury) to 10 (killed) for the others.

Ceramic pots of 1/8,850 are in size were packed with field soil to the depth of 10 cm. The soil was then removed and sprayed and mixed with 4 and 8 kg/ha A.I. of a wettable powder of each active ingredient of the invention, diluted with 1,000 l/ha. The soil so treated was returned to the pots. Immediately thereafter, seven tubers of purple nutsedge were planted 3 cm deep in the soil.

The herbicidal effects were observed after 30 days and rated in the same manner as in (A).

The results obtained are shown in Table 5 below. Diuron was used as a herbicidal reference.

TABLE 5

| Compound No. | Barnyard Grass 1* | Barnyard Grass 2 | Slender Spikerush 1 | Slender Spikerush 2 | Monochoria 1 | Monochoria 2 | Purple Nutsedge 4 | Purple Nutsedge 8 |
|---|---|---|---|---|---|---|---|---|
| 1 | 10 | 10 | 10 | 10 | 10 | 10 | 9 | 10 |
| 2 | 10 | 10 | 10 | 10 | 10 | 10 | 9 | 10 |
| 3 | 10 | 10 | 10 | 10 | 10 | 10 | 10 | 10 |
| 4 | 10 | 10 | 10 | 10 | 10 | 10 | 9 | 10 |
| 5 | 10 | 10 | 10 | 10 | 10 | 10 | 8 | 9 |
| 6 | 10 | 10 | 10 | 10 | 10 | 10 | 7 | 8 |
| 7 | 10 | 10 | 10 | 10 | 10 | 10 | 10 | 10 |
| 8 | 10 | 10 | 10 | 10 | 10 | 10 | 10 | 10 |
| 9 | 10 | 10 | 10 | 10 | 10 | 10 | 7 | 8 |
| 10 | 10 | 10 | 10 | 10 | 10 | 10 | 8 | 9 |
| 11 | 10 | 10 | 10 | 10 | 10 | 10 | 4 | 7 |
| 12 | 10 | 10 | 10 | 10 | 10 | 10 | 10 | 10 |
| 13 | | | | | | | 10 | 10 |
| 14 | 10 | 10 | 10 | 10 | 10 | 10 | | |
| 15 | | | | | | | 9 | 9 |
| 16 | | | | | | | 8 | 9 |
| 17 | | | | | | | | |
| 18 | | | | | | | 10 | 10 |
| 19 | | | | | | | 8 | 9 |
| 20 | | | | | | | 9 | 9 |
| 21 | | | | | | | 10 | 10 |
| 22 | | | | | | | | |
| 23 | | | | | | | 9 | 10 |
| 24 | | | | | | | 9 | 10 |
| 25 | | | | | | | | |
| 26 | 10 | 10 | 4 | 6 | 10 | 10 | 10 | 10 |
| 27 | 10 | 10 | 10 | 10 | 10 | 10 | 9 | 10 |
| 28 | 10 | 10 | 10 | 10 | 10 | 10 | 8 | 9 |
| 29 | 10 | 10 | 10 | 10 | 9 | 10 | 10 | 10 |
| 30 | 10 | 10 | 10 | 10 | 8 | 10 | 8 | 10 |
| 31 | | | | | | | | |
| 32 | | | | | | | 10 | 10 |
| 33 | | | | | | | 10 | 10 |
| 34 | | | | | | | 10 | 10 |
| 35 | | | | | | | 10 | 10 |
| 36 | 10 | 10 | 10 | 10 | 10 | 10 | 3 | 6 |
| 37 | | | | | | | | |
| 38 | | | | | | | | |
| 39 | 9 | 10 | 7 | 8 | 8 | 10 | | |
| 40 | 10 | 10 | 10 | 10 | 10 | 10 | 10 | 10 |
| 41 | 10 | 10 | 10 | 10 | 10 | 10 | 9 | 10 |
| 42 | | | | | | | | |
| Diuron | 10 | 10 | 10 | 10 | 10 | 10 | 1 | 3 |

*kg/ha

TEST 5

Ceramic pots of 1/8,850 are in size were packed with field soil to the depth of 10 cm. The soil was then removed and sprayed and mixed with 1, 2, 4 and 8 kg/ha A.I. of a wettable powder of each active ingredient of the invention, diluted with 1,000 l/ha. The soil so treated was returned to the pots. Immediately thereafter, four tubers of yellow nutsedge were planted 3 cm deep in the soil.

The herbicidal effects were observed after 30 days by means of weighing the fresh weight of the terrestrial portion.

The results obtained are shown in Table 6 below.

TABLE 6

| | 22 Fresh Weight of Terrestial Portion | | | |
|---|---|---|---|---|
| Compound No. | 1* (g (%)) | 2 (g (%)) | 4 (g (%)) | 8 (g (%)) |
| 1 | 19.15 (59) | 6.20 (19) | 2.55 (8) | 1.25 (4) |
| 2 | 5.30 (16) | 1.50 (5) | 0 (0) | 0 (0) |
| 3 | 2.70 (8) | 0.30 (1) | 0.05 (0) | 0 (0) |
| 5 | 28.60 (89) | 11.10 (34) | 0 (0) | 0.05 (0) |
| 6 | 23.20 (72) | 12.40 (38) | 5.30 (16) | 0.70 (2) |
| 7 | 0.10 (0) | 0.10 (0) | 0 (0) | 0 (0) |
| 8 | 2.20 (7) | 0.90 (3) | 0.35 (1) | 0.15 (0) |
| 9 | 35.50 (110) | 12.50 (39) | 2.60 (8) | 0.80 (2) |
| 10 | 13.50 (42) | 3.90 (12) | 1.45 (5) | 1.05 (3) |
| 11 | 37.80 (117) | 32.20 (100) | 6.65 (21) | 6.40 (20) |
| Comparison | | | | |
| 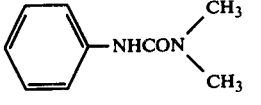 | 31.80 (98) | 30.20 (93) | 24.30 (75) | 14.35 (44) |
| 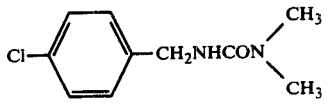 | 33.00 (102) | 34.20 (106) | 30.80 (95) | 35.80 (111) |
| 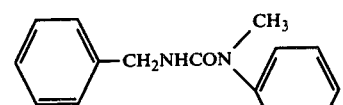 | 34.95 (108) | 39.00 (120) | 37.80 (117) | 31.60 (98) |
| 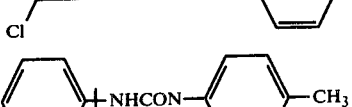 | 29.45 (91) | 25.45 (79) | 19.75 (61) | 4.70 (15) |
| 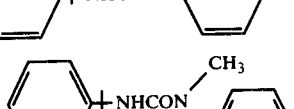 | 6.25 (19) | 8.10 (25) | 2.15 (7) | 1.10 (3) |

TABLE 6-continued

| | 4.75 (15) | 1.30 (4) | 0 (0) | 0 (0) |
|---|---|---|---|---|

Note:
*kg/ha
Control 32.30 g (100%)

The designation "$+$" means $-\underset{\underset{CH_3}{|}}{\overset{\overset{CH_3}{|}}{C}}-$ .

The preparation, formulation and particle size of the wettable powders, aqueous suspensions, dusts, granules, emulsifiable concentrates and solutions in solvents are well known to those skilled in the art. The wettable powders and emulsifiable concentrates can be marketed as formulations containing about 10 to 80% by weight, usually about 50% by weight, of the compounds of this invention, and are diluted optionally with water prior to use. The minimum concentration of the compound in these formulations can be about 0.1% by weight. On the other hand, granules and dusts can be marketed as formulations containing the compounds of this invention in a concentration of about 5 to 80% by weight and prior to use, a solid filler is added as required, and they are applied as formulations containing a surface active agent, with about 5 to 10% by weight of the compound of this invention. Formulations containing other than the above quantities of active ingredient can easily be prepared by those skilled in the art. Application methods of the herbicidal compositions of this invention to the soil and/or plant are well known to those skilled in the art and may be effected by applying the composition to the surface of the soil with or without a solid carrier or by employing a liquid carrier to accomplish penetration and impregnation. According to the present invention, preplant soil incorporation treatment and pre-emergence treatment are preferred rather than foliar treatment (i.e., treatment of above-ground portions of plants) and post-emergence treatment, respectively. Thus, phytotoxicity by germination- and growth-inhibition is greater than with contact phytotoxicity. The application of herbicidal formulations to the surface of soil or the above-ground portions of plants can be carried out by any conventional method, e.g., by powder dusters, by boom and hand sprayers, by spray dusters and by cultivators.

In order to control weed growth, the herbicidal composition of this invention is preferably applied so that about 0.1 to about 20 kg, preferably 0.2 to 10 kg, of the compound of this invention is distributed per hectare of the locus to be treated.

While the invention has been described in detail and with reference to specific embodiments thereof, it will be apparent to one skilled in the art that various changes and modifications can be made therein without departing from the spirit and scope thereof.

What is claimed is:

1. A compound of the general formula (I):

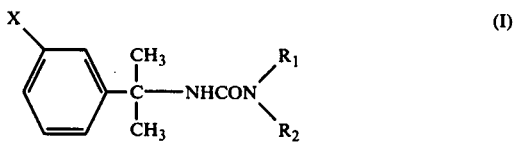

wherein X is halogen or trifluoromethyl, $R_1$ is methyl or methoxy and $R_2$ is $C_4$–$C_5$ alkyl, cyclohexyl or phenyl.

2. The compound of claim 1, wherein said compound is 3-(m-chloro-α,α-dimethylbenzyl)-1-methyl-1-n-butylurea, 3-(m-chloro-α,α-dimethylbenzyl)-1-methyl-1-cyclohexylurea, 3-(m-chloro-α,α-dimethylbenzyl)-1-methyl-1-phenylurea, 3-(m-chloro-α,α-dimethylbenzyl)-1-methoxy-1-phenylurea, 3-(m-trifluoromethyl-α,α-dimethylbenzyl)-1-methyl-1-n-butylurea, 3-(m-trifluoromethyl-α,α-dimethylbenzyl)-1-methyl-1-phenylurea, or 3-(m-trifluoromethyl-α,α-dimethylbenzyl)-1-methoxy-1-phenylurea.

* * * * *